United States Patent [19]

Schiller et al.

[11] Patent Number: 4,783,167

[45] Date of Patent: Nov. 8, 1988

[54] FINGER IMAGING APPARATUS USING CURVED PLATEN

[75] Inventors: Michael Schiller, Riverdale; Daniel H. Marcus, New City, both of N.Y.

[73] Assignee: Fingermatrix, Inc., North White Plains, N.Y.

[21] Appl. No.: 46,906

[22] Filed: May 5, 1987

[51] Int. Cl.⁴ .............................................. G06K 9/20
[52] U.S. Cl. .......................................... 356/71; 382/4
[58] Field of Search ............................. 356/71; 382/4

[56] References Cited

U.S. PATENT DOCUMENTS

| 4,553,837 | 11/1985 | Marcus ................................. | 356/71 |
| 4,681,435 | 7/1987 | Kubota et al. ....................... | 356/71 |

FOREIGN PATENT DOCUMENTS

60-50406  3/1985  Japan .................... 356/71

Primary Examiner—Vincent P. McGraw
Attorney, Agent, or Firm—McAulay, Fields, Fisher, Goldstein & Nissen

[57] ABSTRACT

A curved cylindrical segment platen has a concave touching surface. An interrogating slit light beam is scanned around the platen to scan a finger held against the touching surface. An optical imaging system images the zone illuminated onto an array of photo-transducers to provide a signal representing the fingerprint. The optical system is rotated around the platen. The axis of the interrogating light beam is substantially normal to the touching surface. The axis of the imaging system is off normal by about 56 degrees, an amount which is greater than a critical angle equal to the maximum angle of refraction in the platen. This critical angle is approximately 41 degrees. The axis of the imaging system is also off normal to the non-touching surface by an angle that is less than this critical angle of 41 degrees and thus less than the angle of total internal reflection. As a consequence, the image at the photo-transducers provides a completely dark valley zone and a sharply contrasting light image ridge zone. In a second embodiment, a thick flat platen has a flat touching surface and an opposed parallel flat surface through which an illuminating light beam is applied to scan across a finger applied to the touching surface. The illuminating beam is normal to the touching surface. The axis of the imaging system is at an angle of approximately 50 degrees to the normal, an angle that is thus well past 41 degrees, the maximum angle of refraction. The platen has a side face which is at an angle of 45 degrees to the touching surface. The imaging axis emerges from this sloping side face at an angle to the normal that is substantially less than the angle of total internal reflection.

11 Claims, 4 Drawing Sheets

FINGER IMAGING APPARATUS USING CURVED PLATEN

BACKGROUND OF THE INVENTION

This invention relates in general to an optically generated finger image apparatus and, more particularly, to an apparatus which generates an image from an optical scan of a finger object supported on a platen.

In the art of optical finger image processing, it is desirable to keep the system relatively inexpensive and the size of the system as small as possible while ensuring that the reliability of the system is maintained. In order to get a useful fingerprint image, the contrast between ridge and valley signals must be as great as possible and the background signal must be kept as low and as steady as possible. Further, the apparatus must provide a high resolution image of the fingerprint object.

U.S. Pat. No. 4,322,163 discloses one example of a fingerprint apparatus for generating a fingerprint image to be encoded into machine readable signals. An interrogating slit light beam of substantially collimated light impinges on a finger pressed against a flat platen. The interrogating light beam is at an off normal angle and is displaced across the platen. The finger held on the platen modulates the interrogating light beam to provide a reflected light beam with fingerprint information. The axis of the reflected light beam and the axis of the interrogating light beam are at mirror angles to the normal.

The modulated light beam is imaged onto an array of photo-electric transducers to produce a series of output signals corresponding to the modulated information. The output of the array is serially interrogated at successive scan positions to provide a set of signals containing fingerprint information.

Fingerprint apparatus capable of generating a roll fingerprint image are known in the art. An example having a curved finger retaining platen, is described in U.S. Pat. No. 4,533,837, issued Nov. 19, 1985. That apparatus also employs a collimated interrogating slit light beam at an off normal axis and a modulated reflected light beam at a mirror off normal axis to provide an information signal which is converted to an electrical signal at a photo-electric array.

In addition to the known flat platen and curved platen arrangements there are apparatus which employ a triangular prism as the platen for supporting the finger being interrogated. U.S. Pat. No. 4,210,899 is an example of such an apparatus. Where a prism platen is employed, the interrogating light beam is off normal at an angle of 45 degrees and the axis of the reflected or reading light beam is a mirror image thereof about normal and this is also off normal at 45 degrees.

In all three types of arrangements, five percent (5%) of the incident light is reflected from under the valley/glass interface, obeying the law of reflection, along a mirror axis. About ninety-five percent (95%) of the light passes through the touching surface to be reflectively scattered from the valleys. The ridges of the finger held against the platen effectively squelch geometric reflection because the finger oil on the ridges tends to match the glass index of refraction. Thus, virtually all the light rays headed toward the finger ridges actually contact the ridges and are reflectively scattered back into the glass. The fact that the ridges are substantially in contact with the touching surface and the valleys are not, causes a significant difference in the angular scatter from ridge and valleys. One major difference is that the valley scatter is angularly bounded in space where the ridges are not. This will be later expanded upon.

A second difference is that the five percent (5%) valley/glass interface reflection lies along the mirror axis and the ridge reflection is scattered so that none of the ridge reflection coincides with the same mirror axis. Thus, along the mirror axis, the light is pure valley light and an optical system with an effective aperture approaching zero diameter would only receive valley signals. Such a design would force a system "f" number approaching infinity and thus would have substantially no resolution. Therefore, lens apertures with reasonable dimensions will receive the geometrically reflected five percent (5%) light as well as sufficiently equal ridge and valley scatter to cause a varying signal base line substantially greater than the five percent valley zone light along the mirror axis.

Accordingly, it can be seen that in these fingerprint optical reading systems, the axis of the imaging segment is the mirror image of the axis of the interrogating segment. That is, if the axis of the interrogating light beam is twenty degrees off normal, the axis of the imaging or reading system will also be twenty degrees to the normal in order for the optical aperture of the imaging segment to be centered on the reflected light beam and pick up as much of the 5% of the light that is reflected along the mirror line as possible. Nonetheless, the fact that some 95% of the incident light is reflected in a scattered fashion (as contrasted with along a mirror line) by the valley and ridge zones, means a substantial undesirable background is provided against which it is difficult to pick out the valley signal.

In addition, latent images further obscure the desired image. Finger oil left by previous applications of fingers to the platen provide an image which tends to scatter some of the 5% of light reflected from the valley interface and increase the difficulty of distinguishing the valley signal.

This latent image problem and other related problems were resolved by a technique disclosed in pending U.S. patent application Ser. No. 630,012 filed July 12, 1984, and entitled Direct Finger Reading. The optical fingerprint image generating apparatus disclosed therein does not employ a platen. The finger object is held in position and its surface interrogated by a coherent, collimated light beam. The light beam is preferably shaped in the form of a slit extending along the length of the finger surface being interrogated. The slit beam is scanned around the finger in a rotational motion. The reflected modulated light beam is focused onto a linear array of photo-responsive transducers to provide an electrical signal image of the optical image focused on the array. A limitation on the image so provided is a tendency to lose focus and thus lose image definition and information during a portion of the scan. This out-of-focus problem arises for two reasons. First, the finger being scanned is not a perfect cylinder and, thus, the object position varies along the optical axis. Second, the thickness of the different individual fingers varies greatly so that the extent of the out-of-focus conditions will vary from individual to individual.

Accordingly, an object of this invention is to provide a fingerprint image having high contrast between ridge and valley zones.

Another object of this invention is to provide such an apparatus which avoids swamping out the fingerprint signal with a base line or background signal.

Another object to this invention is to provide this high contrast signal with minimum base line such that the image formed is in focus across the length and width of the finger being interrogated.

A further object of the invention is to provide apparatus which is relatively inexpensive, which is reliable, which provides a repeatable image and which is relatively small in size.

It is an object of this invention to meet the various objects stated above in a device that will be effective with the wide range of finger shapes that exist in the population.

BRIEF DESCRIPTION

In one embodiment of the invention, a moderately thick (for example, 5 mm) curved platen is provided. The platen has a finger receiving cylindrical concave "touching" surface and a cylindrical convex surface. These two surfaces are spaced from each other by the thickness of the platen.

An interrogating light beam in the form of a slit illuminates a slit zone of a finger applied to the touching surface. The finger on the touching surface provides reflected light modulated with the image of the finger surface that is illuminated.

An imaging lens optically downstream focuses the illuminated finger zone onto a linear array of photo-electric transducers. The optical axis of the imaging lens intersects the platen at a point substantially off the mirror axis. This imaging optical axis intersects the platen in a relatively narrow zone. On one side of this narrow zone is the standard reading area where the emergent light is composed of the five percent (5%) mirror axis valley light mixed with reflected scatter from the valleys and additional reflected scatter from the ridges. On the other side of this narrow zone there is no emergent light because the light reflectively scattered from the ridges is totally internally reflected. The imaging optical axis images the ridges on the photo-electric array as light images and images the valleys as the complete absence of light.

There is a cone about the normal to the touching surface of the platen in which the emergent light includes that five percent (5%) which is geometrically reflected from the air-in-valley/glass interface and which also includes light reflectively scattered from the ridges and all of the reflectively scattered light from the valleys. The axis of the interrogating light beam lies in this cone so that the light reflected along the mirror axis will be within the cone.

The emergent light from this cone is specifically excluded from the optical aperture of the imaging system of this invention by positioning the axis of the imaging system outside of that cone. The area that includes reflected scattered ridge light which is totally internally reflected provides no emergent light and thus cannot contribute to the image at the array of photo-electric transducers. Between those two areas is a limited area in which the emergent light is solely light reflected from the ridges. Between those areas is where the axis of the reading system extends.

This is in sharp contrast with the prior art flat platen and curved platen devices where the axis of the imaging system is positioned within the cone and in particular positioned to be at the mirror image to the normal of the axis of the interrogating light beam.

The interrogating light beam as well as the imaging lens and the array are all mounted on a bracket for rotation about the axis of the platen to provide a scan of the fingerprint image across the array. The optical axis of the interrogating light beam is maintained perpendicular to the zone being interrogated throughout this rotational scan.

BRIEF DESCRIPTION OF THE DRAWINGS

FIG. 7 is an optical schematic of a second embodiment of this invention employing a flat platen. FIG. 7 is a side view.

DEFINITIONS

Optical Axis. The refraction of light as it passes from one medium (air or glass) to the other (glass or air) causes the light to bend away from the normal as the light goes from glass to air and toward the normal as light goes from air to glass. It should be understood herein that reference to the optical axis of a light beam is to that line which includes the bend. Thus, the optical axis is not a straight line because of the change in the index of refraction of the media through which the light beam passes. Most importantly herein, the modulated or reading light beam that is defined by the optical aperture of the focusing lens and the photo-diode array extends along an axis that bends at the non-touching surface of the platen. Thus, reference herein to the optical axis of the reading light beam shall be understood to refer to the dogleg line that bends at the non-touching surface of the platen.

Reading Light Beam. The reading light beam is the beam of light which is focused on the array. It is not all of the light reflected from the finger being interrogated. It is not all of the light which emerges from the platen. It is only that portion of the light which is collected by the aperture of the focusing lens and projected onto the photo-diode array. In particular, the reading light beam does not include that light which is totally internally reflected. It does not include that light which is reflected along the mirror axis; that is along an axis which has the same angle to the normal as does the interrogating light beam. And, it does not include certain other reflected light which is not received within the aperture of the focusing lens.

TIR. The acronym TIR will be used in place of the phrase "total internal reflection" in various circumstances in the specification and claims. The term "TIR angle" refers to an angle at which the internal light rays do not emerge from the platen. At the TIR angle or greater, light rays within the platen which are incident at the surface of the platen are internally reflected. The angle is measured between the normal to the surface and the path of the internal rays which impinge on the surface. By contrast, light rays within the platen which are at an angle to the normal less than the TIR angle are partially reflected and partially transmitted. The TIR angle for glass in an air ambient environment is approximately 41 degrees.

MAR. The acronym MAR stands for Maximum Angle of Refraction. Light incident on the glass platen will be deflected as it is transmitted through the glass platen because of the difference in the index of refraction of air and the glass of the platen. The refraction causes the incident light ray to be bent toward the normal. The amount by which the light ray is bent is determined by Snell's Law. An incident light ray which is normal to the surface of the platen is not bent. The more the incident light ray deviates from the normal the more it is bent. At a limit case, an incident light ray which is parallel to the surface of the platen will be bent more than any other incident ray. The angle such a limit ray makes with the normal within the glass is termed herein the "maximum angle of refraction" or MAR. The MAR angle for glass in an air environment is approximately 41 degrees. No ray incident on the platen will have an angle to the normal in the platen greater than the 41 degree MAR.

Figure 5:
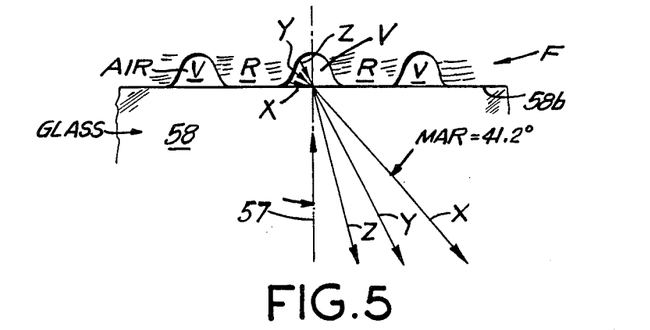
FIG. 5 is an optical schematic illustration showing the cone in the platen which contains all the light reflectively scattered from the valley surfaces.

Critical Angle. The MAR angle and the TIR angle are the same angle. They are derived from the same basic relationships dictated by Snell's Law. That angle will be called herein the Critical Angle. As seen in FIG. 5, because of this Critical Angle, light incident on the touching surface that is reflectively scattered from the valleys will all be contained within a cone around the normal. This cone has a half angle equal to the Critical Angle. The source of the light which causes the spatially bounded valley scatter is the light which is not the five percent (5%) that is reflected at the glass to air-under-valley interface. Instead, it is the light that is transmitted through the interface onto the valley surface and reflected from the valley surface. Because of this Critical Angle, all rays which scatter from the valley surface and re-enter the touching surface 18b (see FIG. 3) cannot form an angle greater than the MAR/-TIR with the normal, which normal is the radius to the surface 18b. Thus, all valley scatter is bounded within the cone whose half angle maximum ray intersects the non-touching surface 18a at point C. Thus, the Critical Angle at 18b determines the area on the convex surface 18a within which the emergent light will contain (a) the five percent (5%) light which is geometrically reflected from the interface under the valleys, (b) scattered light reflected by the valleys and (c) some of the scattered light reflected by the ridges. The Critical Angle at surface 18a also determines the area beyond which no ridge scattered light emerges from the platen. For a flint glass platen operating in air, this Critical Angle is 41.2 degrees.

DESCRIPTION OF THE PREFERRED EMBODIMENTS

Figure 2:
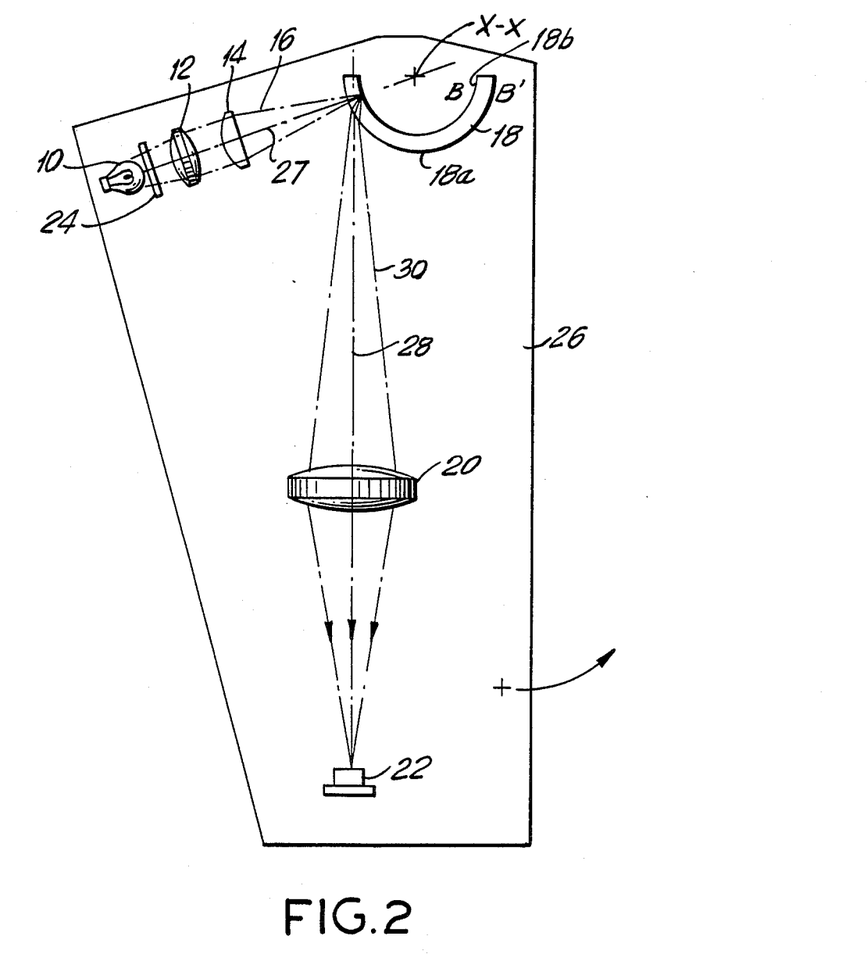
FIG. 2 is an optical and mechanical schematic representation of the FIG. 1 apparatus.

As shown in the FIGS., one embodiment of this invention employs an incandescent white light source 10. A spherical lens assembly 12 and planoconvex cylindrical condensing lens 14 form the light into an interrogating light beam 16 which impinges on the finger F as a slit beam of light. FIG. 2 shows a view looking at an end of the curved transparent glass platen 18. In that view, the length of the slit light beam 16 extends in a direction perpendicular to the plane of the paper.

The concave surface 18b is the touching surface. That is, surface 18b is the surface against which the finger F is placed. The illuminated portion of the finger F is focused by the imaging lens 20 onto a linear photo-diode array 22.

In one embodiment that has been tested, the lamp 10 is a 7.5 watt miniature incandescent bulb and the array 22 is a charge coupled diode (CCD) array comprising 2,048 photo-diode cells that extend along a line that is perpendicular to the plane of FIG. 2.

In that embodiment the condensing lens 12 is an aspheric condensing lens having a forty mm focal length positioned about 40 mm in front of the light source, the lens 14 is a cylindrical condensing lens positioned about 6 mm downstream from lens 12 and about 25 mm upstream from the point A. The slit light beam at the touching surface 18b is approximately two mm wide. In that embodiment, the imaging lens 20 has a 50 mm focal length and is approximately 135 mm downstream from the surface 18b and approximately 80 mm upstream from the array 22.

It might be noted that an alternate embodiment which has been tested provides operable results with a light source 10 composed of a linear array of four infrared emitting diodes (IRED) aligned along a line substantially parallel to the axis X—X. In that embodiment, four 8 mm focal length lenses are employed for the condensing lens assembly 12, one of those lenses being downstream from each of the four light sources. The resulting light pattern of four overlapping circles is condensed by the lens 14 to the slit interrogating light beam at surface 18b. The main advantage of the single incandescent bulb light source 10 is that it has a greater light intensity than do the IREDs.

Figure 1:
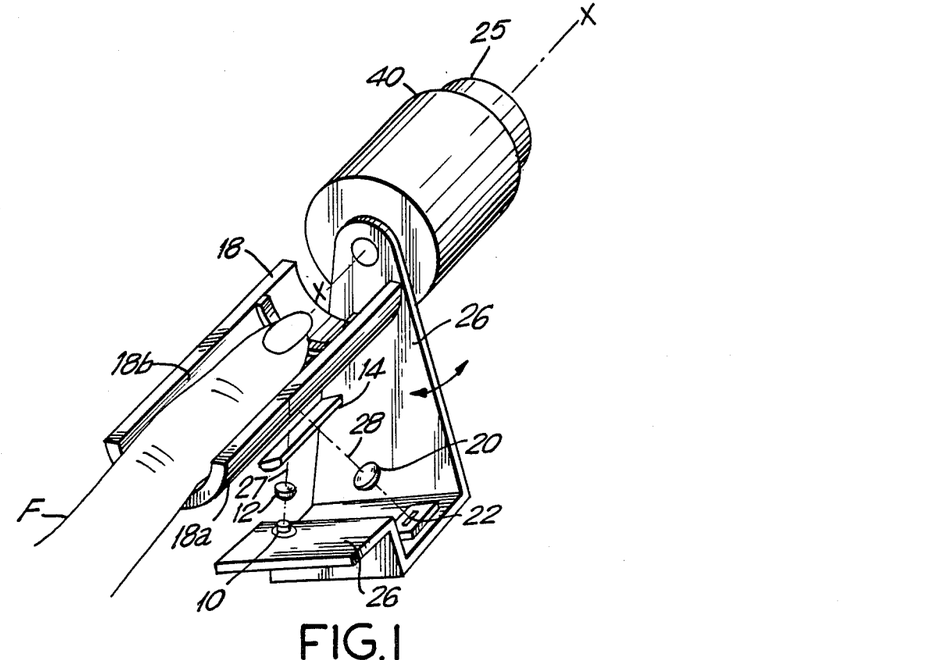
FIG. 1 is a perspective view of a curved platen embodiment of the apparatus of this invention with a finger in place to be read.

A diffuser element 24 such as the one disclosed in U.S. Pat. No. 4,569,080 issued Feb. 4, 1986 is placed downstream from the light source 10 to assure that the interrogating light beam 16 does not carry any images such as, for example, the image of the filament. For presentation purposes, the diffuser 24 is not shown in FIG. 1.

The entire optical assembly, except for the platen 18, constitutes an optical interrogating and detecting unit. That unit is mounted on a rotatable support 26 so that the interrogating light beam 16 can be rotated around the finger about the axis X—X. As the interrogating slit light beam 16 rotates about the finger F the image on surface 18a is scanned. Thus, a complete roll fingerprint image is scanned across the array 22.

Figure 4:
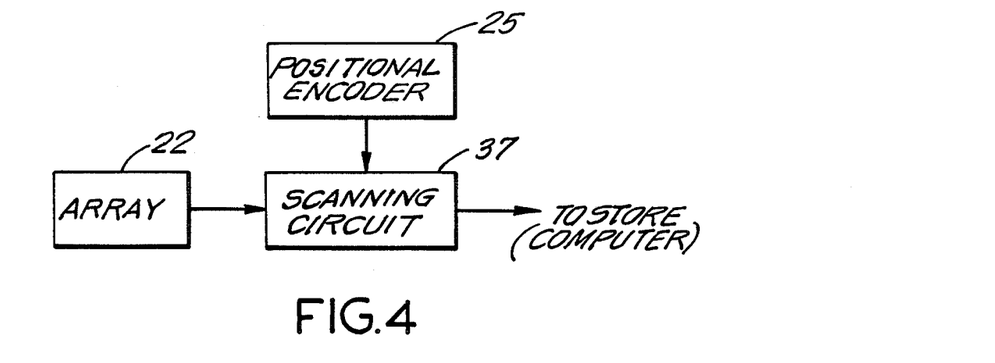
FIG. 4 is a block diagram illustrating the arrangement for electronically scanning the optical image to provide a two-dimensional set of pixel values representing the fingerprint image.

As motor 40 rotates the support 26, then as indicated in FIG. 4, a positional encoder 25 produces the signal for each predetermined incremental angular advance of the optical interrogating and detecting unit. The signal is applied to scanning circuit 37 which interrogates array 22 in response to each signal. Scanning circuit 37 provides an output signal each time array 22 is interrogated. The output signal is representative of the fingerprint information at each position where the array 22 is interrogated. Elements of the scanning apparatus are conventional and are similar to those described in issued U.S. Pat. No. 4,322,163.

The platen 18 has its concave touching surface 18b as a segment of a circular cylinder, the center of which is at the axis X—X. Similarly, the outer convex surface 18a is a segment of a circular cylinder. In one embodiment, the radius of the touching surface 18b is approximately 11.8 mm (464 mils) and the radius of the non-touching or convex surface 18a is about 16.1 mm (635 mils) for a platen thickness of 4.3 mm. In that embodiment, the length of the platen 18 is approximately 57 mm (2.25 inches).

Figure 3:
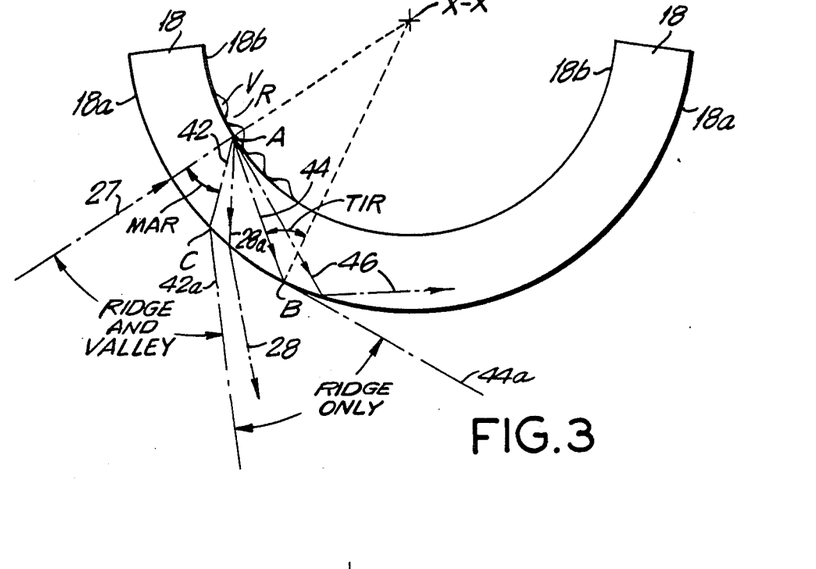
FIG. 3 is an enlarged cross-sectional view of the cylindrical platen of the FIG. 1 apparatus overlaid with illustration of the geometric relations involved in the FIG. 1 embodiment.

FIG. 3 is an enlarged view of the cross section of the platen 18 that is shown in FIG. 2 and indicates the nature of the relationship between the interrogating light beam 16 and the reading light beam 30. It shows that the axis 28 of the reading light beam 30 is not the mirror of the axis 27 of the interrogating light beam 16.

The geometry of the arrangement of the curved platen is illustrated in FIG. 3. As shown therein, the interrogating light beam is along an axis 27 which is a radius of the circular surfaces 18a and 18b and thus the axis 27 is normal to the surface at the illuminating zone A. The reading light beam has an off-normal axis 28. The axis 28 steers away from the normal as it emerges from the platen 18 since it is passing from the optically denser glass medium of the platen 18 to the less dense medium of the air. The portion of the axis 28 in the platen is labelled 28a.

It is critical that the reading axis 28 intersect the non-touching surface 18a between the points C and B as indicated on FIG. 3. Between these points C and B, emergent rays carry only ridge information and absolutely no valley information. The emergent rays between these two points C and B are rays which are scattered from the ridge surface only. Accordingly, the image that is focused onto the array 22 by the lens 20 is one in which the valley zones exhibit complete absence of light, thereby providing maximum contrast between the valley zones and the ridge zones. In brief, the point B is determined by the point at which the reflected scattered rays from the ridges are totally internally reflected within the platen 18. The point C is determined by the limit of the zone on the surface 18a which includes all light reflected from the valleys. Thus, from the FIG. 3 viewpoint (i) no reflected light emerges from the surface 18a to the right of the point B and (ii) light reflected from both valleys and ridges emerges from the surface 18a to the left of the point C.

Assume the platen 18 is crown glass having an index of refraction of 1.517. The index of refraction for air is presumed to be 1.0. Thus, the light reflected back off the valleys of the finger will be incident on the surface 18b and will be refracted within the platen 18 by being bent toward the normal. The amount by which the incident ray reflected from the valley is bent toward the normal is determined by Snell's Law. If one assumes that an incident ray in a limit case, is parallel to the surface 18b, then for a crown glass platen, that ray will be bent toward the normal such that its angle with the normal within the platen 18 will be approximately 41.2 degrees. Any incident ray having an angle less than 90 degrees to the normal will refract such that its angle to the normal within the platen 18 will be less than 41.2 degrees. Accordingly, 41.2 degrees is the maximum angle of refraction and is shown on FIG. 3 as the angle MAR.

FIG. 5 illustrates this significant aspect of the basic optics involved. FIG. 5 diagrammatically shows the valleys V and ridges R of a finger F pressed against a flat surface 58b of a glass platen 58. The axis 57 of the interrogating beam is normal to the surface 58b. The portion of the interrogating light that is not reflected along the mirror axis is transmitted through to impinge on the valley area of a finger F. As the light strikes the irregular surface of the valley V, it is scattered back toward the platen surface 58b at all angles. Three rays are shown. The first ray x is substantially parallel to the surface 58b. Thus, where it enters the surface 58b, it is refracted such that the ray x within the glass platen 58 is at an angle of 41.2 degrees to the normal 57. The second and third rays y and z are at lesser angles to the normal in the air in the valley area V and thus are at lesser angles to the normal in the glass platen 58 than is the limit ray x. The limit ray x corresponds to the line 42 in FIG. 3. Thus, it can be seen that all light reflected from under the valleys will be contained within a cone around the normal 57 which cone has a half angle of 41.2 degrees.

Accordingly, all valley zone information will be contained in reflected rays which are in this MAR zone.

By contrast with the valley zones V, the ridges R are in intimate optical contact with the touching surface 18b. Finger oil has an index of refraction approximately that of glass. It serves to fill in the intensities between the ridge surface and the platen surface 18b so that there is no mismatch under the ridge and thus no interface mirror image reflection. What does occur at the ridge zones R is that the irregular finger surface scatters the reflected light at all angles to provide the ridge image which is focused onto the array 22 along the axis 28.

Because the axis 28 of the reading light beam 30 in the FIG. 2 embodiment is at an angle to the normal at the interrogating line A that is greater than the maximum angle of refraction, none of the information that is contained within the reading light beam 30 is valley information. As a consequence, the image at the array 22 provides an extremely dark, zero light level valley zone image The result is a substantial contrast between valley zone imagery and ridge zone imagery to provide a much more usable and useful image downstream from the array 22.

The line 44 in FIG. 3 illustrates a further limitation of the reading axis 28. Light from the line of interrogation A which represents ridge information will be scattered by the ridge over a substantial angle of scatter. A ray of light along the line 44 will emerge at a tangent to the surface 18a as shown at 44a. The line 44 is defined by the TIR angle. Any light in the platen 18 which is reflected with an angle to the normal at surface 18a that is greater than the TIR angle will not emerge from the surface 18a. It will be totally internally reflected. The ray 46 illustrates a TIR ray. Accordingly, the reading axis portion 28a must intersect the surface 18a with an angle to the normal that is less than the TIR angle. Where the platen 18 is flint glass having an index of refraction of 1.517 and where the environment in which it operates is air, this TIR critical angle is 41.2 degrees. Thus, the reading axis portion 28a that is in the platen must intersect the touching surface 18b with an angle to the normal that is greater than 41.2 degrees and must intersect the non-touching surface 18a with an angle to the normal that is less than 41.2 degrees. The signal processed by the focusing lens 20 and array 22 will carry ridge and only ridge information. That is all the light in the reading beam 30 will be light from the ridge zones and, most importantly, none of the light in the reading beam 30 will be from the valley zones.

It should be kept in mind that the axis 27 of the interrogating light beam is conveniently and preferably oriented so that it is normal to the surface 18b. However, it can be off normal without significantly changing the relationships involved. The maximum angle of refraction MAR will still be 41.2 degrees to the normal. Further, the angle of the interrogating light beam will not affect the line 44 which defines the smallest angle at which total internal reflection occurs. Essentially, the axis 27 of the interrogating light beam must be kept out of the zone between the lines 42 and 44, recognizing that both of these lines in FIG. 3 represent a conical surface.

The representation in FIG. 3 is to light rays along a cross section perpendicular to the axis X—X. This provides a legitimate analysis because it is a limit case in that rays which are reflected or scattered from a point along the zone A will follow the same rules with respect to a plane parallel to FIG. 3. Further, the line 42, defines a conical zone of rotation about the axis 27 for the point along the line A represented in FIG. 3. The set of lines 42 from each point on the line A defines a plane extending between the line A and a line at C, which line at C extends along the surface 18a perpendicular to the plane of FIG. 3.

The important point to remember is that there is a zone of emergent light at the non-touching surface 18a between B and C which contains only light reflected from the ridges As seen in FIG. 3, emergent light to the left of C will contain light reflected from the valley zones as well as light reflected from the ridge zones and the area to the right of B will contain no emergent light. Of course, as the interrogating light beam in axis 27 rotates about the cylindrical axis X—X, the points A, C and B rotate correspondingly so that the geometric relations just described remain constant throughout the rotational scan.

In use, a number of different sized platens 18 are provided to accommodate different size fingers.

Figure 6:
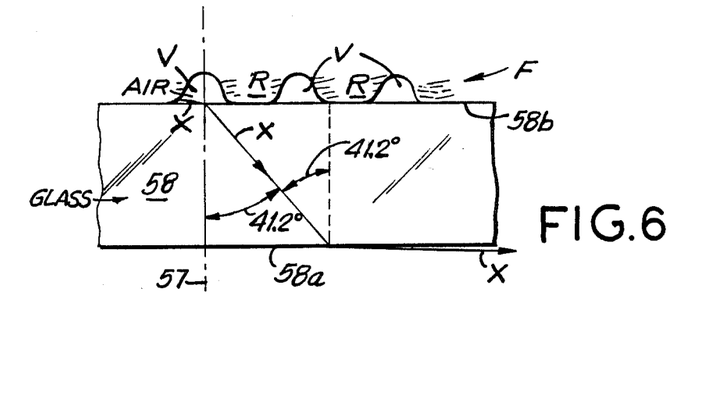
FIG. 6 is an optical schematic similar to FIG. 5 showing why in a flat glass platen there is no zone between the zone of mixed ridge and valley reflection and the zone of total internal reflection.

FIG. 6 illustrates why this invention cannot be applied to a flat platen situation. FIG. 6 is an optical schematic similar to that of FIG. 5 except that the non-touching surface 58a of the platen is included. Since the surface 58a is parallel to the surface 58b, the limit ray x within the platen will have the same angle to the normal at surface 58a as it has to the normal at surface 58b. Since this angle is the critical angle 41.2 degrees, it means that the ray x will be internally reflected. As a limit case, the ray x could be considered to emerge from the surface 58a at an angle parallel to the surface 58a. In any case, it is clear that all rays having an angle greater than 41.2 degrees will be totally internally reflected. As a consequence, the only imagery that can emerge from the surface 58a of the flat platen is imagery contained with the cone around the normal 57 which is limited by the MAR angle. The light within that cone will include light reflected from the valley zones and light reflected from the ridge zones and thus is a mixture of ridge and valley information. It is this that provides the background base line that makes it difficult to extract the five percent light that is reflected from the surface 58b which is under the valley zones V.

Figure 7:
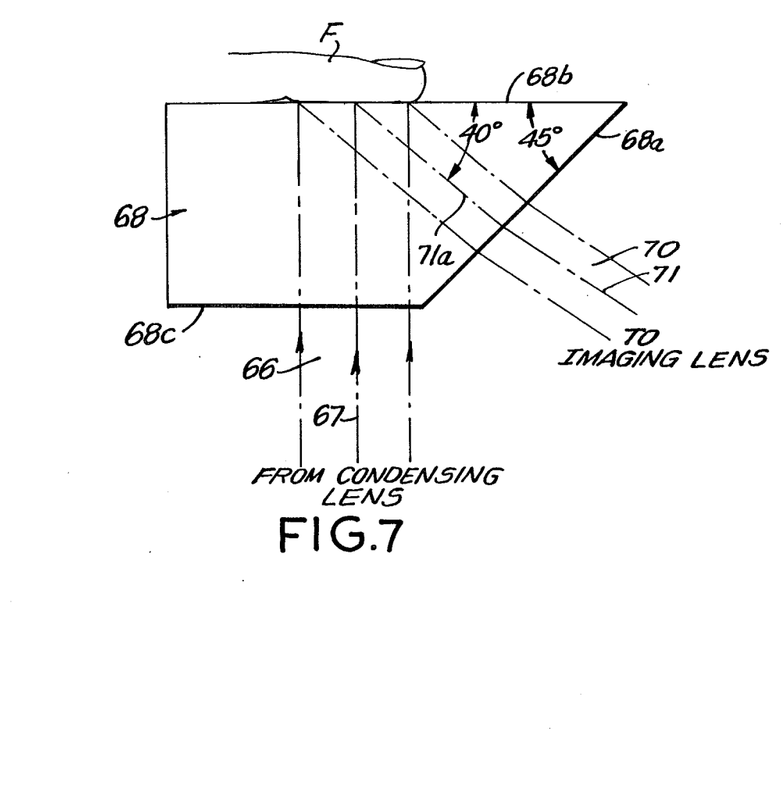
Figure 8:
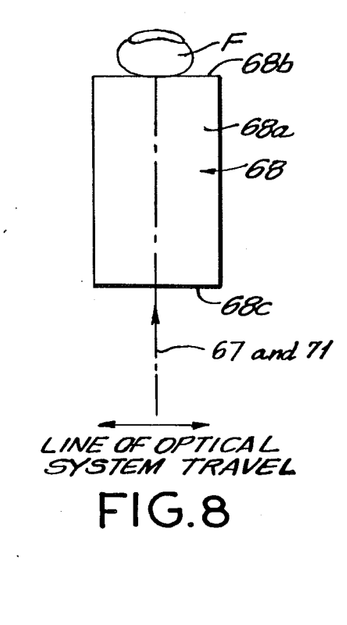
FIG. 8 is an optical schematic end view of the FIG. 7 apparatus.

FIGS. 7 and 8 are optical schematic views of a second embodiment of this invention in which a finger F is placed on the touching surface 68b of a glass platen 68. The platen 68 has a non-touching surface 68a from which the reflected modulated light emerges. The interrogating light beam 66 in the form of a slit light beam is generated by the same type of source and lenses as are shown in the FIG. 2 embodiment. The axis 67 of the interrogating light beam 66 is preferably substantially normal to the touching surface 68b.

The analysis of what happens in the valleys and ridges of the finger F at the touching surface 68b is substantially the same as is the analysis of what happens at the touching surface 18b in the FIG. 2 embodiment. That is, light reflected from the air to glass interface under the valleys is reflected along a mirror axis. Light scattered from the valley surfaces is all reflected within a cone having an axis that is normal to the surface 68b and whose half angle is equal to the critical angle, namely 41.2 degrees.

The reading beam 70 is composed of modulated reflected light along the imaging axis 71. The portion 71a of the axis that is within the platen 68 is at an angle of forty degrees to the plane of the touching surface 68b and thus this portion 71a is at an angle of fifty degrees to the normal at the touching surface 68b. This puts the axis of the reading beam 70 outside of the cone defined by the critical angle. As a consequence, none of the scattered light from under the valleys is present in the reading light beam 70. And, of course, the light reflected at a mirror angle from the interface is directed back along the axis 67. Thus, only scattered reflected light from the ridges is in the reading light beam 70.

The surface 68a from which the reading beam 70 emerges is at an angle of 45 degrees to the touching surface 68b and thus the axis 71a of the reading beam has an internal angle to the normal of five degrees with the emergent surface 68a and is well within the critical angle at which total internal reflection occurs.

It might be noted that the interrogating light beam 66 enters the platen 68 through the surface 68c which is parallel to the surface 68b. Since the beam 66 is normal to the touching surface 68b it is within the cone defined by the maximum angle of refraction which is the critical angle. In order to assure that the entire modulated reading beam 70 emerges, it is necessary that the emergent surface 68a be sufficiently long to encompass the entire modulated beam and thus the platen 68 has to be quite thick. In one embodiment it is approximately five centimeters thick.

The angle of 45° between the touching surface 68b and the emergent surface 68a was selected because of the convenience in fabrication. The angle could vary appreciably as long as the angle to the normal of the emergent beam 70 within the platen 68 is less than the critical angle so as to avoid total internal reflection of the scattered light from the ridges.

The reading light beam 70 is further processed by an imaging lens such as shown in FIG. 2 so that the image scanned at the surface 68b is approximately focused onto an array of photo-detectors such as shown in FIG. 2. The entire interrogating optical arrangement and imaging optical arrangement from lamp to photo-transducers (except for platen 68) is mounted on a platform (not shown) so that it can travel along a line parallel to the plane 68b. The line of travel is perpendicular to the plane of FIG. 7 and parallel to the plane of FIG. 8. An arrangement such as shown in U.S. Pat. No. 4,544,267 could be employed for this purpose. However, any support bracket mounted for linear motion in the proper direction can be employed. And, of course, the reading of the CCD array on which the light beam is focused involves the same units as shown in FIG. 4.

In known prism platen arrangements, the axis of the imaging system is at an angle of 45 degrees to the normal. It is the mirror axis of the interrogating light beam which is at 45 degrees to the normal. This 45 degree angle means that the axis of the reading light beam is outside of the cone defined by the critical angle discussed earlier. But, since the reading is along the mirror axis, the geometrically reflected signal from the air-in-valley to glass interface is adulterated with light scattered from the ridges. The light scattered from the ridges creates a significant base line against which makes it difficult to distinguish between the light reflected from the air-in-valley to platen interface and the ridge scatter reflected light.

When an object is tilted to the imaging optical axis, certain known adjustments are made to provide an appropriate focus of the object on the image surface. In the FIG. 7 embodiment, the slit zone being illuminated is tilted to the optical axis 71 and therefore the CCD array 22 must be tilted to coincide with the image that will be formed due to the tilted nature of the object. This is a known imaging technique.

It should be noted that the image line will be foreshortened and distorted. This may or may not require compensation in the system. A readjustment of overall magnification provides a first order compensation for the foreshortening effect, but such will change the magnification in the orthogonal axis. The combination of unequal magnification and distortion will produce an unsymmetric pixel. The line scan increments will preserve the shape of the image. The use of an anamorphic lens as the imaging lens 20 is one known technique to minimize the effect of the unequal magnification. It might be noted that in this FIG. 7 embodiment, the unequal glass path lengths will also contribute to scale distortion and may require additional focus adjustment and system compensation.

FIG. 8 illustrates this embodiment as one in which one finger F is interrogated. It is contemplated that this FIG. 7 embodiment could usefully be employed to interrogate four fingers of a hand placed on the platen 68. In that application the width of the platen 68 is much greater than is shown in FIG. 8.

What is claimed is:

1. In an optical fingerprint imaging system having an interrogating light beam for illuminating a finger placed against a platen to provide a modulated reflected light beam, the system having an imaging segment for imaging the reflected beam onto a photo-electric transducer, the improvement comprising:
   a curved platen having a concave finger touching surface and a convex non-touching surface through which the modulated reflected light beam emerges,
   the imaging segment having an axis within a zone in the platen bounded by a first plane having an angle to the normal at said touching surface equal to the critical angle and a second plane having an angle to the normal at said non-touching surface equal to the critical angle,
   the interrogating light beam having an axis within the platen such that its mirror axis is outside of said zone,
   the axis of said interrogating light beam intersecting said non-touching surface.

2. The apparatus of claim 1 wherein said curved platen is a cylindrical platen having said touching surface as a concave cylindrical surface and said non-touching surface as a convex cylindrical surface.

3. The apparatus of claim 2 further comprising:
   optical means for shaping said interrogating light beam to provide an interrogating zone at said touching surface in the form of a slit, the long axis of said slit being parallel to the axis of said cylindrical touching surface, and
   means for rotating the interrogating light beam and the imaging segment and transducers about said axis touching surface to provide an optical scan of a finger placed at said touching surface.

4. The apparatus of claim 3 wherein:
   the optical axis of said interrogating light beam is substantially normal to said touching surface.

5. The apparatus of claim 1 wherein said interrogating light beam is a slit light beam having its long axis aligned with the axis of the finger applied to the platen.

6. In a fingerprint processing apparatus having an interrogating light beam for interrogating a finger having ridge and valley zones to provide a reflected reading light beam and having imaging means including photo-electric transducers coupled to said reading light beam, to provide an electrical signal at the transducers representative of a fingerprint, the improvement comprising:
   a curved platen positioned in the interrogating light beam, said platen having a first curved surface as a touching surface, a second curved surface as a non-touching surface spaced from said touching surface, a finger placed on said touching surface being illuminated by said interrogating light beam, the optical axis of said interrogating light beam having an internal angle to the normal at said touching surface that is less than the maximum angle of refraction for said platen,
   the optical axis of said imaging means having a first internal angle to the normal at said touching surface and a second internal angle to the normal at said non-touching surface, said first angle being greater than the maximum angle of refraction for said platen and said second angle being less than the angle of total internal reflection for said platen,
   the axis of said interrogating light beam intersecting said non-touching surface.

7. The apparatus of claim 6 wherein:
   said platen is a cylindrical platen, said touching surface being a concave cylindrical surface and said non-touching surface being a convex cylindrical surface.

8. The apparatus of claim 7 further comprising:
   optical means for shaping said interrogating light beam to provide an interrogating zone at said touching surface in the form of a slit, the long axis of said slit being parallel to the axis of said cylindrical touching surface, and
   means for rotating the interrogating light beam and the imaging segment and transducers about said axis of said touching surface to provide an optical scan of a finger placed at said touching surface.

9. The apparatus of claim 8 wherein:
   the optical axis of said interrogating light beam is substantially normal to said touching surface.

10. The apparatus of claim 6 wherein said interrogating light beam is a slit light beam having its long axis aligned with the axis of the finger applied to the platen.

11. The method of optically imaging a finger held against the surface of a platen onto a photo-electric transducer comprising the steps of:

scanning an interrogating light beam across a finger held against a concave curved touching surface of a curved platen, said light beam having an angle to the normal within said platen at said curved touching surface which is less than the critical angle, to provide a modulated reflected light beam which emerges from a convex curved non-touching surface of the platen, imaging the modulated reflected light beam onto the photo-electric transducer along an axis that has an angle to the normal within said platen at said touching surface which is greater than the critical angle and an angle to the normal within said platen at the non-touching surface which is greater than the critical angle.

* * * * *